(12) United States Patent
Ooyauchi et al.

(10) Patent No.: US 10,434,265 B2
(45) Date of Patent: Oct. 8, 2019

(54) MEDICAL HOLLOW NEEDLE ASSEMBLY AND METHOD OF MANUFACTURING HOLLOW NEEDLE

(71) Applicant: TERUMO KABUSHIKI KAISHA, Tokyo (JP)

(72) Inventors: Tetsuya Ooyauchi, Yamanashi (JP); Kenta Gotou, Yamanashi (JP); Yukio Imai, Yamanashi (JP); Hidenori Fujiwara, Yamanashi (JP); Madoka Horie, Yamanashi (JP); Hideo Kawamoto, Yamanashi (JP); Ayumi Kumagai, Gifu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/065,526

(22) Filed: Mar. 9, 2016

(65) Prior Publication Data
US 2016/0184532 A1      Jun. 30, 2016

Related U.S. Application Data

(63) Continuation of application No. PCT/JP2014/004656, filed on Sep. 10, 2014.

(30) Foreign Application Priority Data

Sep. 11, 2013   (JP) ................................. 2013-188358
Sep. 11, 2013   (JP) ................................. 2013-188362

(51) Int. Cl.
*B23K 31/02*     (2006.01)
*A61M 5/34*      (2006.01)
(Continued)

(52) U.S. Cl.
CPC ............ *A61M 5/343* (2013.01); *A61M 5/158* (2013.01); *A61M 5/329* (2013.01); *B21G 1/08* (2013.01);
(Continued)

(58) Field of Classification Search
CPC ...... A61M 5/343; A61M 5/329; A61M 5/158; A61M 5/346; A61M 5/345;
(Continued)

(56) References Cited

U.S. PATENT DOCUMENTS 1,705,763 A * 3/1929 Hasbrouck ............. D06B 11/00
                                                  604/272
2,081,038 A * 5/1937 Keller .................... B21D 51/00
                                                   29/33 Q
(Continued)

FOREIGN PATENT DOCUMENTS

DE      3045411 A1 * 7/1982
EP      1 547 635 A1   6/2005
(Continued)

OTHER PUBLICATIONS

International Search Report for PCT/JP2014/004656 dated Nov. 25, 2014.
(Continued)

*Primary Examiner* — Kiley S Stoner
(74) *Attorney, Agent, or Firm* — Foley & Lardner LLP

(57) ABSTRACT

A medical hollow needle assembly includes an outer cylindrical body including a through-hole; a hollow needle having an outer peripheral surface, wherein a proximal portion of the hollow needle is disposed in the through-hole of the outer cylindrical body, and wherein the outer peripheral surface of the hollow needle has an outer reduced-diameter surface that has a smaller outer diameter than that of a more proximal portion of the outer peripheral surface of the
(Continued)

hollow needle; and an inner cylindrical body including an insertion hole in which the hollow needle is disposed, wherein the inner cylindrical body is disposed between the hollow needle and an inner peripheral surface of the through-hole of the outer cylindrical body, and wherein the inner cylindrical body joins the outer cylindrical body and the hollow needle.

10 Claims, 15 Drawing Sheets

(51) Int. Cl.
- *A61M 5/158* (2006.01)
- *A61M 5/32* (2006.01)
- *B21G 1/08* (2006.01)
- *B23K 101/06* (2006.01)

(52) U.S. Cl.
CPC ............ *B23K 31/027* (2013.01); *A61M 5/345* (2013.01); *A61M 5/346* (2013.01); *A61M 2207/00* (2013.01); *B23K 2101/06* (2018.08)

(58) Field of Classification Search
CPC ....... A61M 2207/00; B21G 1/08; B23K 1/14; B23K 5/02; B23K 9/0253; B23K 11/062; B23K 11/063; B23K 11/0873; B23K 11/0876; B23K 13/025; B23K 13/046; B23K 26/262; B23K 31/027; B23K 2101/04–12
USPC ............................. 228/17, 17.5, 141.1–265
See application file for complete search history.

(56) References Cited

U.S. PATENT DOCUMENTS

| | | | | |
|---|---|---|---|---|
| 2,416,391 A * | 2/1947 | Hixson | ................ | A61M 5/162 137/588 |
| 2,844,149 A | 7/1958 | Getting | | |
| 3,289,675 A * | 12/1966 | Eby | ..................... | A61M 5/3286 604/272 |
| 3,570,086 A * | 3/1971 | Stone | .................... | B21D 31/043 29/6.2 |
| 3,581,041 A * | 5/1971 | Balfanz, Jr. | ............. | B21C 37/08 219/60 R |
| 4,409,046 A | 10/1983 | Holzwarth et al. | | |
| 4,747,835 A * | 5/1988 | Sandhaus | ........... | A61M 5/3213 604/192 |
| 4,819,325 A * | 4/1989 | Cross | ....................... | B23H 1/04 219/69.15 |
| 4,922,076 A * | 5/1990 | Cross | ....................... | B23H 1/04 219/69.15 |
| 5,085,639 A * | 2/1992 | Ryan | .................... | A61M 5/3243 604/110 |
| 6,007,474 A * | 12/1999 | Rydell | ................ | A61N 5/1007 600/7 |
| 6,592,287 B1 * | 7/2003 | Hagle | .................. | B23K 1/0008 228/258 |
| 6,877,652 B2 * | 4/2005 | Ooyauchi | ............... | B21C 37/06 228/170 |
| 2002/0035828 A1 * | 3/2002 | Chia | ....................... | A44C 11/00 59/80 |
| 2002/0052580 A1 | 5/2002 | Ooyauchi | | |
| 2002/0138042 A1 * | 9/2002 | Llorach | .................. | A61M 5/343 604/187 |
| 2003/0211352 A1 * | 11/2003 | Ooyauchi | ............. | B21C 37/065 428/600 |
| 2004/0035176 A1 * | 2/2004 | Haase | ..................... | B21B 17/00 72/368 |
| 2006/0264827 A1 | 11/2006 | Whang | | |
| 2008/0053181 A1 | 3/2008 | Frauchiger | | |
| 2008/0103430 A1 * | 5/2008 | Gomez | ............... | A61F 9/00745 604/20 |
| 2009/0292243 A1 * | 11/2009 | Harding | ............ | A61M 25/0618 604/110 |
| 2009/0299291 A1 * | 12/2009 | Baid | .................... | A61M 5/3273 604/164.08 |
| 2012/0116322 A1 * | 5/2012 | Brink | .................. | A61B 10/0233 604/264 |
| 2012/0253297 A1 * | 10/2012 | Matsuzawa | ........... | A61M 5/158 604/272 |
| 2014/0236102 A1 | 8/2014 | Matsumoto et al. | | |
| 2015/0148757 A1 * | 5/2015 | Aeschlimann | ........ | A61M 5/158 604/272 |
| 2016/0175540 A1 * | 6/2016 | Johnson | ............... | A61M 5/3221 604/198 |

FOREIGN PATENT DOCUMENTS

| | | | |
|---|---|---|---|
| FR | 2718967 A | * | 10/1995 |
| GB | 0 354 767 A | | 8/1931 |
| GB | 0 361 594 A | | 11/1931 |
| JP | S64-067949 A | | 3/1989 |
| JP | 2004-154210 A | | 6/2004 |
| JP | 2006-329382 A | | 12/2006 |
| JP | 2007-054194 A | | 3/2007 |
| JP | 2007-283132 A | | 11/2007 |
| WO | WO-2009/091895 A2 | | 7/2009 |
| WO | WO-2013/027799 A1 | | 2/2013 |
| WO | WO-2013/065370 A1 | | 5/2013 |

OTHER PUBLICATIONS

English Translation of Chinese Office Action in application No. 201480050017.6.
Extended European Search Report dated Oct. 12, 2017 in corresponding application No. 14844372.4.
English Translation of International Preliminary Report on Patentability dated Mar. 15, 2016 in corresponding application No. PCT/Jp2014/004656.
English Translation of Japanese Office Action in corresponding application No. 2015-536449.

* cited by examiner

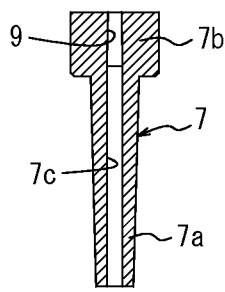
FIG. 3A
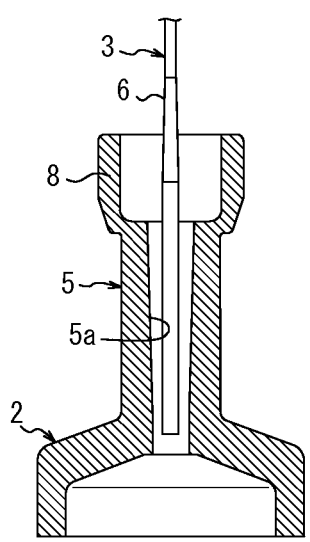
FIG. 3B
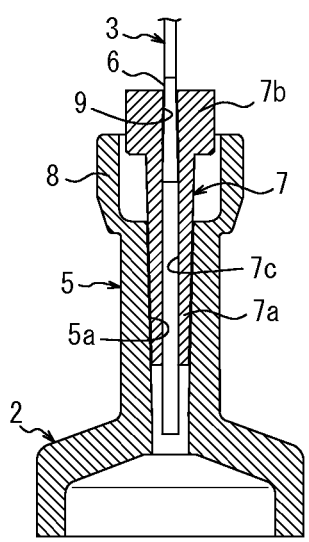
FIG. 3C
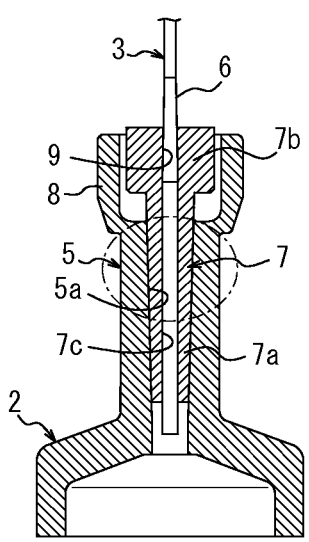

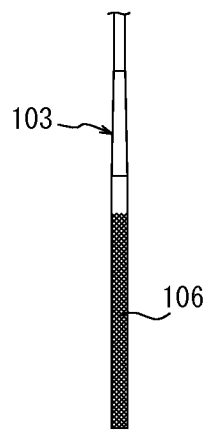
FIG. 10A
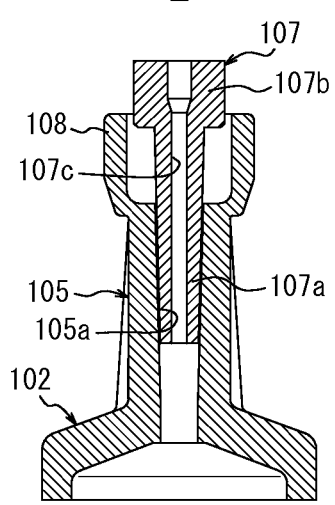
FIG. 10B
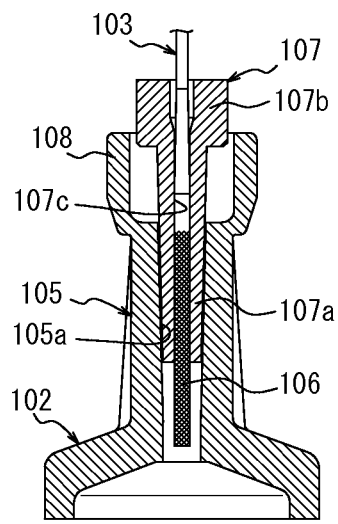
FIG. 10C
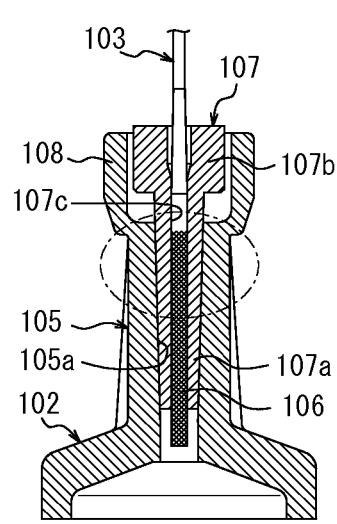

MEDICAL HOLLOW NEEDLE ASSEMBLY AND METHOD OF MANUFACTURING HOLLOW NEEDLE

CROSS-REFERENCE TO RELATED APPLICATIONS

This application is a continuation application filed under 35 U.S.C. § 111(a) claiming the benefit under 35 U.S.C. §§ 120 and 365(c) of PCT International Application No. PCT/JP2014/004656, filed on Sep. 10, 2014, which is based upon and claims the benefit of priority of Japanese Application No. 2013-188358 and Japanese Application No. 2013-188362, both filed on Sep. 11, 2013. The contents of all of these applications are hereby incorporated by reference in their entireties.

BACKGROUND OF THE INVENTION

Technical Field

The present disclosure relates to a medical hollow needle assembly obtained by joining a hollow metal needle to a resin outer cylindrical body, such as a syringe with a needle, an injection needle, an indwelling needle, or a butterfly needle, and further to a method of manufacturing a hollow needle used for a medical instrument.

Background Art

Syringes with needles have been used as medical instruments for injection, blood sampling, or the like to or from a living body such as a human body. As a syringe with a needle, a syringe with a fixed needle and a syringe with a detachable needle are known. A syringe with a fixed needle is configured so that a hollow metal needle is directly joined to a port of a resin syringe body. A syringe with a detachable needle is configured so that an injection needle is obtained by joining a hollow metal needle to a distal end of a resin hub (needle hub), and the hub is joined to a port of a syringe body. In an injection needle used for such a syringe with a fixed needle or a syringe with a detachable needle, the hollow metal needle is joined to the port of the syringe body or a resin outer cylindrical body such as the hub, and is configured as a hollow needle assembly. In this configuration, the hollow needle is configured so that an outer peripheral surface of a proximal end side portion of the hollow needle is joined to an inner peripheral surface of the port of the syringe body or an inner peripheral surface of the resin cylindrical body such as the hub, and the hollow needle is fixed to the cylindrical body.

As a method of manufacturing a hollow needle used for such a medical instrument, the following method is known. The method includes punching out a plate body having a predetermined shape from a metal plate such as a stainless steel sheet, rolling the plate body in a mold to be molded into a tubular body, joining a seam portion of the molded tubular body by welding, bonding, or the like, and forming the hollow needle.

In order to prevent removal of the hollow needle from the outer cylindrical body and secure safety, such a hollow needle assembly or a medical instrument must have the hollow needle joined to the outer cylindrical body with a joint strength not less than a predetermined value relative to a tensile load. Therefore, a configuration for joining the hollow needle and the outer cylindrical body with an adhesive has been generally employed. However, in this configuration, the adhesive used for joining is likely to make contact with a drug solution, blood, or the like to change the quality of the drug solution or negatively impact a human body, and there is a problem that in a joining step, checking process, or the like, the presence or absence of adhesion of the adhesive to the hollow needle or the like needs to be strictly managed.

Therefore, for example, as disclosed in JP 2004-154210 A, a configuration has been proposed that involves fixedly press-fitting an inner cylindrical body having a tapered outer surface and inserting one end of a hollow needle therein into a through-hole of an outer cylindrical body, in which an outer peripheral surface of the one end of the hollow needle is roughened by blasting or the like to cause an anchor effect on a joining surface, and the hollow needle is rigidly joined to the inner cylindrical body without an adhesive.

In this configuration, a plate body punched out from a metal plate is molded into a tubular body by pressing, a seam portion thereof is joined to form a hollow needle, and the outer peripheral surface of the hollow needle is further subjected to blasting. Thus, the anchor effect is generated at a joining portion between the hollow needle and the cylindrical body, and the hollow needle is rigidly joined to the cylindrical body without an adhesive.

SUMMARY OF INVENTION

However, in the configuration as disclosed in JP 2004-154210 A, where the outer peripheral surface of the hollow needle is subjected to roughening and the roughened portion is only brought into close contact with an inner peripheral surface of the inner cylindrical body, the configuration has difficulty in sufficiently increasing the joint strength of the hollow needle with respect to the outer cylindrical body, relative to a tensile load.

Furthermore, in a method of subjecting the outer peripheral surface of the hollow needle to blasting for roughening, foreign matter, such as a projection material used for the blasting or broken pieces caused by the blasting may attach to the outer peripheral surface or the inside of the processed hollow needle, and therefore, a countermeasure against the foreign matter is required.

Furthermore, it is difficult to integrate the blasting having a risk of attachment of the foreign matter to the hollow needle or a peripheral environment with another process such as a pressing step or a joining step, and therefore, a blasting step is required to be added after the pressing step or the joining step for manufacturing the hollow needle, and thus, a manufacturing process of a hollow needle is disadvantageously increased in steps.

Embodiments of the present invention have been made in view of such a problem, and an object of certain embodiments of the present invention is to provide a medical hollow needle assembly which is increased in joint strength of a hollow needle with respect to an outer cylindrical body, relative to a tensile load.

Furthermore, another object of certain embodiments of the present invention is to provide a method of manufacturing a hollow needle by which a manufacturing process can be simplified, and attachment of foreign matter to a hollow needle can be prevented.

A medical hollow needle assembly according to one embodiment of the present invention includes an outer cylindrical body including a through-hole, a hollow needle having an outer peripheral surface partially including an outer reduced-diameter surface having a diameter reduced toward a distal end side, and having a proximal end side disposed in the through-hole, and an inner cylindrical body including an insertion hole through which the hollow needle is inserted, being disposed between the hollow needle and the inner peripheral surface of the through-hole, and joining the outer cylindrical body and the hollow needle. The insertion hole of the inner cylindrical body is provided with an inner reduced-diameter surface being reduced in diameter toward the distal end side, and engaging the outer reduced-diameter surface of the hollow needle.

In the medical hollow needle assembly according to one aspect, each of the outer reduced-diameter surface and the inner reduced-diameter surface are formed as a tapered surface having a diameter gradually reduced toward a distal end side.

In the medical hollow needle assembly according to another aspect, the inner reduced-diameter surface is provided to be extended from a distal end opening of the insertion hole.

In the medical hollow needle assembly according to another aspect, the outer reduced-diameter surface and the inner reduced-diameter surface are formed as a perpendicular surface perpendicular to an axial direction of the through-hole.

In the medical hollow needle assembly according to another aspect, preferably, the outer cylindrical body and the inner cylindrical body is formed of a resin material, the inner cylindrical body fuses between the hollow needle and the inner peripheral surface of the through-hole, and the hollow needle is joined to the outer cylindrical body.

In the medical hollow needle assembly according to another aspect, the inner cylindrical body is preferably formed by combining a plurality of segmented pieces obtained by being divided along a division plane passing through an axis of the insertion hole.

In the medical hollow needle assembly according to another aspect, preferably, the inner cylindrical body preferably has a C-shaped cross-section and includes, in a side portion, a needle insertion slit extending from the insertion hole, and the inner cylindrical body is formed to be deformed to close the needle insertion slit.

In the medical hollow needle assembly according to another aspect, the outer cylindrical body is preferably a port of a syringe.

In the medical hollow needle assembly according to another aspect, the outer cylindrical body is preferably a hub that is connectable to a connection portion of a medical instrument.

A method of manufacturing a hollow needle according to another embodiment of the present invention is a method of manufacturing a hollow needle used to be joined to an inner peripheral surface of a cylindrical body provided in a medical instrument. The method includes a pressing step comprising punching out a plate body having a predetermined shape from a metal plate, and rolling the plate body to be molded into a tubular shape, and a joining step comprising joining a seam portion of the plate body having been molded into the tubular shape. A surface of the plate body is roughened in the pressing step to provide a roughened portion on at least part of an outer peripheral surface of a portion to be joined to the inner peripheral surface of the cylindrical body of the hollow needle.

In the method of manufacturing a hollow needle according to another aspect, the surface of the plate body is preferably roughened, when the plate body is punched out from the metal plate.

In the method of manufacturing a hollow needle according to another aspect, the surface of the plate body is preferably roughened, when the plate body is rolled into the tubular shape.

In the method of manufacturing a hollow needle according to another aspect, the roughened portion preferably has a diamond knurl.

In the method of manufacturing a hollow needle according to another aspect, the roughened portion preferably has an annular groove extending in a circumferential direction of the hollow needle.

In the method of manufacturing a hollow needle according to another aspect, the hollow needle preferably is a tapered needle having an outer diameter reduced from a proximal end side toward a distal end side.

In the method of manufacturing a hollow needle according to another aspect, preferably, the medical instrument is a syringe, and the cylindrical body is an inner cylindrical body inserted into a port of the syringe to join the hollow needle to the port.

According to certain embodiments of the present invention, the insertion hole of the inner cylindrical body through which the hollow needle is inserted is provided with the inner reduced-diameter surface to engage the outer reduced-diameter surface, which is provided on the outer peripheral surface of the hollow needle, with the inner reduced-diameter surface. Thus, the engagement between the inner reduced-diameter surface and the outer reduced-diameter surface allows the hollow needle to lock to the inner cylindrical body joined to an inner surface of the outer cylindrical body, in a removal direction, and a joint strength of the hollow needle with respect to the outer cylindrical body can be increased relative to a tensile load.

According to certain embodiments of the present invention, in the pressing step, the surface of the plate body is roughened to provide the roughened portion at least partially on the outer peripheral surface of the portion joined to the inner peripheral surface of the cylindrical body of the hollow needle. Thus, a step of providing the roughened portion on the outer peripheral surface of the hollow needle does not need to be provided separately from the pressing step or the joining step, and the manufacturing process of a hollow needle can be simplified. Furthermore, the roughened portion can be provided on the outer peripheral surface of the hollow needle without the blasting in the pressing step, thus preventing the attachment of the foreign matter to the hollow needle being completed. Accordingly, a method of manufacturing a hollow needle can be provided which simplifies the manufacturing process and prevents the attachment of the foreign matter to the hollow needle.

BRIEF DESCRIPTION OF THE DRAWINGS

FIGS. 3A to 3C are schematic diagrams illustrating a procedure of joining a hollow needle to a port of a syringe body.

FIGS. 10A to 10C are schematic diagrams illustrating a procedure of joining a hollow needle to a port of a syringe body.

DESCRIPTION OF EMBODIMENTS

An embodiment of the present invention will be exemplified and described below with reference to the drawings.

Figure 1:
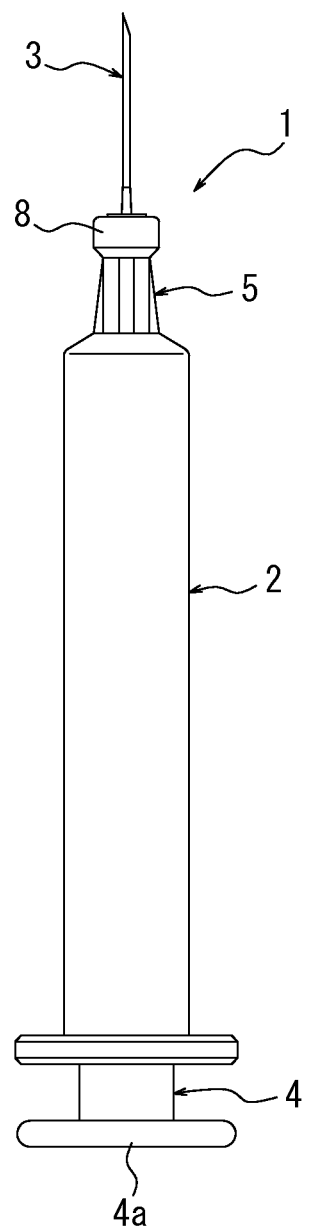
FIG. 1 is a front view of a syringe with a fixed needle according to an embodiment of the present invention.

FIG. 1 illustrates a syringe 1 with a fixed needle according to an embodiment of the present invention (medical hollow needle assembly). The syringe 1 with a fixed needle is used as a medical syringe for injecting a drug solution such as vaccine into a living body such as a human body, and includes a syringe body 2 and a hollow needle (cannula) 3.

The syringe body 2 is formed of a resin material, is formed as a cylindrical shape, and a piston 4 including an operation piece 4a is axially movably mounted in the syringe body 2. The inside of the syringe body 2 is partitioned by the piston 4, and defined as a liquid chamber. The liquid chamber can store the drug solution. The resin material forming the syringe body 2 can include, for example, cyclic polyolefin or polycarbonate.

Figure 2:
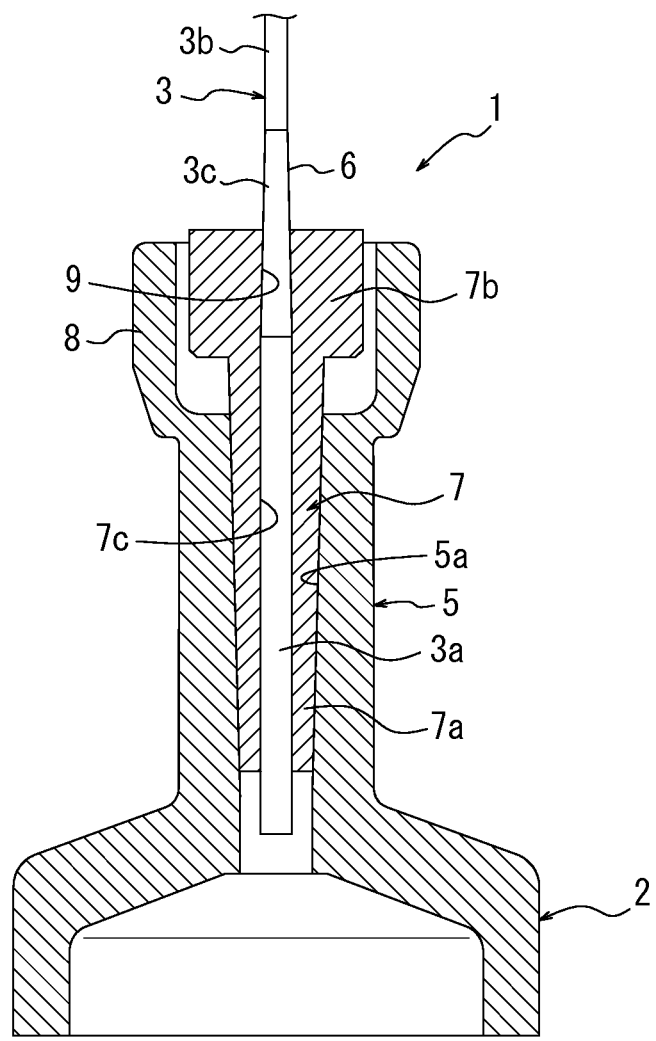
FIG. 2 is an enlarged cross-sectional view illustrating an enlarged main portion of the syringe with a fixed needle of FIG. 1.

A cylindrical port (outer cylindrical body) 5 serving as an outlet for a drug solution is provided at one axial end of the syringe body 2. The cylindrical port 5 is formed of the same resin as the syringe body 2, and is provided integrally with the syringe body 2. As illustrated in FIG. 2, the port 5 is axially provided with a through-hole 5a, the through-hole 5a extends along the axis of the syringe body 2, and is formed as a tapered hole having an inner diameter gradually reduced from a distal end side toward a proximal end side of the port 5.

Meanwhile, the hollow needle 3 is formed of a metal, is formed as an elongated cylindrical shape axially including a flow channel (not illustrated), and has a distal end cut, for example, obliquely to have an acute shape to be inserted into the living body such as a human body. The hollow needle 3 is formed by rolling a metal plate including for example a stainless steel or a titanium alloy by pressing or the like, and joining butted ends thereof, but the hollow needle 3 may be formed of another metal or resin and may be formed by another manufacturing method or the like.

A portion within a predetermined range from a proximal end of the hollow needle 3 is defined as a large diameter portion 3a formed to have a constant outer diameter within the predetermined range, and a portion within a predetermined range from a distal end is defined as a small diameter portion 3b formed to have a constant outer diameter smaller than that of the large diameter portion 3a. A reduced-diameter portion 3c is formed between the large diameter portion 3a and the small diameter portion 3b, and the reduced-diameter portion 3c has an outer peripheral surface formed as an outer reduced-diameter surface 6, and the outer reduced-diameter surface 6 has an outer diameter reduced from a proximal end side toward a distal end side, that is, from the large diameter portion 3a to the small diameter portion 3b. Especially, in the present embodiment, the outer reduced-diameter surface 6 of the hollow needle 3 is formed as a tapered surface (conical surface) having an outer diameter gradually reduced from the proximal end side toward the distal end side.

The hollow needle 3 is disposed coaxially with the through-hole 5a, the large diameter portion 3a being a portion on the proximal end side of the hollow needle 3 is disposed in the through-hole 5a, and the small diameter portion 3b being a portion on the distal end side projects outward from the through-hole 5a. The flow channel provided in the hollow needle 3 communicates with the liquid chamber of the syringe body 2 on the proximal end side, and is opened outward on the distal end side.

A resin inner cylindrical body (inner) 7 is inserted into the through-hole 5a to be positioned between an outer peripheral surface of the hollow needle 3 and an inner peripheral surface of the through-hole 5a, and the port 5 and the hollow needle 3 are joined by the inner cylindrical body 7.

The inner cylindrical body 7 has a main body portion 7a having a tapered outer shape having an outer diameter gradually reduced from a distal end side (upper side in figure) toward a proximal end side (lower side in figure) thereof, and a head portion 7b provided integrally at a distal end of the main body portion 7a, and the main body portion 7a is inserted through the through-hole 5a. The main body portion 7a has an outer peripheral surface formed as a tapered surface having the same tapered angle as the inner peripheral surface of the through-hole 5a, and makes contact with the inner peripheral surface of the through-hole 5a. Furthermore, the inner cylindrical body 7 is axially provided with an insertion hole 7c opened at both axial ends, and the hollow needle 3 is inserted through the insertion hole 7c. The head portion 7b of the inner cylindrical body 7 is formed to have a diameter larger than that of the main body portion 7a, disposed outside the through-hole 5a, and has a lower surface opposed to a distal end surface of the port 5.

The port 5 has a distal end integrally provided with a locking portion 8 for locking a rubber cover (not illustrated) covering the hollow needle 3. The locking portion 8 is formed as a cylindrical shape having a diameter larger than that of the port 5, projects axially from the distal end of the port 5, and covers an outer periphery of the head portion 7b of the inner cylindrical body 7 inserted through the through-hole 5a. The syringe body 2 may have a configuration in which the port 5 is not provided with the locking portion 8.

The main body portion 7a of the inner cylindrical body 7 is pressed into the through-hole 5a, that is, between the hollow needle 3 and the inner peripheral surface of the through-hole 5a while being heated and fused. Thus, in the inner cylindrical body 7, the outer peripheral surface of the main body portion 7a is welded on the inner peripheral surface of the through-hole 5a, an inner peripheral surface of the insertion hole 7c of the main body portion 7a makes close contact with the outer peripheral surface of the hollow needle 3, and the port 5 and the hollow needle 3 are joined to each other. In this configuration, the main body portion 7a of the inner cylindrical body 7 can be pressed between the hollow needle 3 and the inner peripheral surface of the through-hole 5a while being fused, for example according to the following procedure.

First, as illustrated in FIG. 3A, the hollow needle 3 is supported by a fixture of the like, and the large diameter portion 3a is disposed at a predetermined position of the through-hole 5a. Next, as illustrated in FIG. 3B, the hollow needle 3 is inserted through the insertion hole 7c of the inner cylindrical body 7, and the main body portion 7a of the inner cylindrical body 7 is inserted into the through-hole 5a. As illustrated in FIG. 3C, an upper surface of the head portion 7b is pressed toward the through-hole 5a by a pressing device or the like while heating the main body portion 7a and the port 5, and the main body portion 7a of the inner cylindrical body 7 is pressed to a predetermined position between the hollow needle 3 and the inner peripheral surface of the through-hole 5a while being fused. Thus, in the inner cylindrical body 7, the outer peripheral surface of the main body portion 7a is welded on the inner peripheral surface of the through-hole 5a, an inner peripheral surface of the insertion hole 7c makes close contact with the outer peripheral surface of the hollow needle 3 to generate an anchor effect, and the port 5 and the hollow needle 3 can be joined to each other. At this time, since the through-hole 5a and the main body portion 7a of the inner cylindrical body 7 are formed as the tapered shape, the diameter of the main body portion 7a is gradually reduced as the pressing progresses. Thus, the main body portion 7a of the inner cylindrical body 7 can be firmly joined to an inner surface of the through-hole 5a or the outer peripheral surface of the hollow needle 3. Note that, in the inner cylindrical body 7, at least part of the outer peripheral surface of the main body portion 7a is preferably welded on the inner peripheral surface of the through-hole 5a, and a welding range or welding position thereof can be arbitrarily set.

In the above method, the inner cylindrical body 7 and the port 5 can be heated, for example, by laser radiation. In this configuration, the hollow needle 3 including the metal is heated by the laser, and then the inner cylindrical body 7 and the port 5 are heated by heat transferred from the hollow needle 3. In the present embodiment, as indicated by a portion enclosed by a dashed line in FIG. 3C, the main body portion 7a pressed between the port 5 and the through-hole 5a is heated within a range of approximately 3 mm from an opening of the through-hole 5a.

Note that a filler including a heat generating material such as a metal may be mixed, or a ring member including the heat generating material such as a metal may be disposed, in the inner cylindrical body 7 or the port 5 to directly heat the inner cylindrical body 7 or the port 5 by laser radiation. Furthermore, means for heating is not limited to laser radiation, and may employ other means, for example, ultrasonic heating or high-frequency heating. Furthermore, a configuration may be employed in which only the inner cylindrical body 7 is heated and the port 5 is not heated.

As described above, while the hollow needle 3 is located at a predetermined position in the through-hole 5a, the inner cylindrical body 7 receiving the insertion of the hollow needle 3 is pressed between the hollow needle 3 and the inner peripheral surface of the through-hole 5a, while being heated and fused by the laser radiation. Thus, the outer peripheral surface of the inner cylindrical body 7 can be accurately welded on the inner peripheral surface of the through-hole 5a. Furthermore, the inner peripheral surface of the insertion hole 7c of the inner cylindrical body 7 can be brought into close contact with the outer peripheral surface of the hollow needle 3 to smooth slight roughness on the outer peripheral surface of the hollow needle 3, and thus, the inner peripheral surface of the inner cylindrical body 7 can be joined to the outer peripheral surface of the hollow needle 3 by the anchor effect. Accordingly, the port 5 and the hollow needle 3 are joined through the inner cylindrical body 7.

Note that, as described above, a process of pressing the inner cylindrical body 7 while heating and fusing allows joining without generating bubbles in the inner cylindrical body 7. Accordingly, the inner cylindrical body 7 accurately fills a gap between the outer peripheral surface of the hollow needle 3 and the inner peripheral surface of the through-hole 5a, and the liquid chamber of the syringe body 2 can be sealed.

Figure 4:
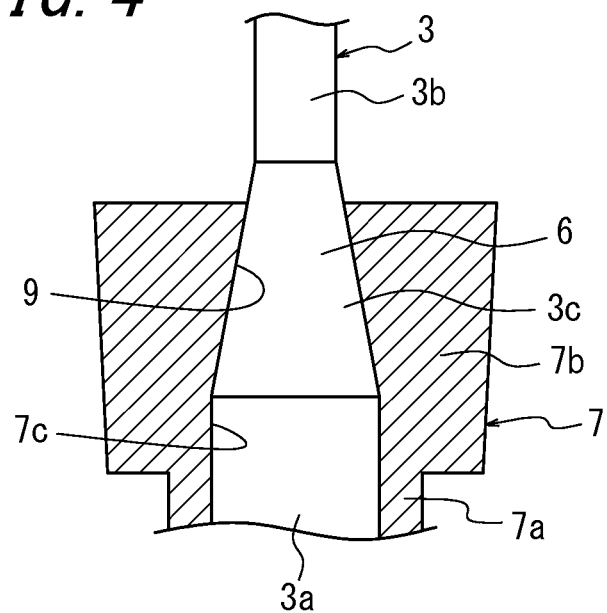
FIG. 4 is an enlarged schematic diagram schematically illustrating an engagement portion between an outer reduced-diameter surface and an inner reduced-diameter surface illustrated in FIG. 2.

The insertion hole 7c of the inner cylindrical body 7 is provided with an inner reduced-diameter surface 9 which has an inner diameter that is reduced. As schematically illustrated in FIG. 4, in the present embodiment, the inner reduced-diameter surface 9 is formed as a tapered surface (conical surface) having an inner diameter gradually reduced from a proximal end side (liquid chamber side) toward a distal end side (outward opening side) of the insertion hole 7c. A tapered angle of the inner reduced-diameter surface 9 is set to be the same as the tapered angle of the outer reduced-diameter surface 6 of the hollow needle 3, and the outer reduced-diameter surface 6 of the hollow needle 3 which is inserted into the insertion hole 7c abuts on the inner reduced-diameter surface 9 of the insertion hole 7c. That is, in the hollow needle 3, the outer reduced-diameter surface 6 is engaged with the inner reduced-diameter surface 9 of the insertion hole 7c in the axial direction. Therefore, the hollow needle 3 is locked to the inner cylindrical body 7 to be prevented from being moved in a removal direction, that is, toward the distal end side.

In the present embodiment, the inner reduced-diameter surface 9 is provided to extend to an opening of the insertion hole 7c positioned on the distal end side of the port 5. In contrast, a portion of the insertion hole 7c other than the inner reduced-diameter surface 9 is formed to have an inner diameter slightly larger than the outer diameter of the large diameter portion 3a of the hollow needle 3. That is, the inner reduced-diameter surface 9 partially constitutes the inner peripheral surface of the insertion hole 7c.

Owing to the above configuration, the hollow needle 3 is locked to the inner cylindrical body 7 in the removal direction by engagement of the outer reduced-diameter surface 6 with the inner reduced-diameter surface 9 of the insertion hole 7c, in addition to the anchor effect caused by close contact of the inner peripheral surface of the inner cylindrical body 7, and the hollow needle 3 is accurately joined to the inner cylindrical body 7. The outer peripheral surface of the inner cylindrical body 7 is welded on the inner peripheral surface of the through-hole 5a, so that the inner cylindrical body 7 to which the hollow needle 3 is firmly joined to the port 5, and the hollow needle 3 is firmly joined to the port 5 through the inner cylindrical body 7.

As described above, in certain embodiments of the present invention, the inner cylindrical body 7 is provided with the inner reduced-diameter surface 9, and the outer reduced-diameter surface 6 provided on the hollow needle 3 is engaged with the inner reduced-diameter surface 9. Thus, the hollow needle 3 is locked to the inner cylindrical body 7 welded on the inner peripheral surface of the through-hole 5a in the removal direction, and the joint strength of the hollow needle 3 to the port 5 can be increased relative to the tensile load.

Furthermore, in certain embodiments of the present invention, the outer reduced-diameter surface 6 of the hollow needle 3 is engaged with the inner reduced-diameter surface 9 of the inner cylindrical body 7 to increase the joint strength of the hollow needle 3 to the port 5, and the joint strength of the hollow needle 3 to the port 5 can be increased, without roughening, such as blasting, the outer peripheral surface of the hollow needle 3 or without bonding the outer peripheral surface of the hollow needle 3 with an adhesive. Accordingly, roughening or bonding with an adhesive is not required to prevent that the adhesive or foreign matter generated upon roughening makes contact with the drug solution in the liquid chamber of the syringe body 2 or the hollow needle 3, and makes a negative influence on the living body such as a human body or the drug solution, and checking or the like for management of the negative influence is not required to reduce the cost of the syringe with a fixed needle.

Figure 5:
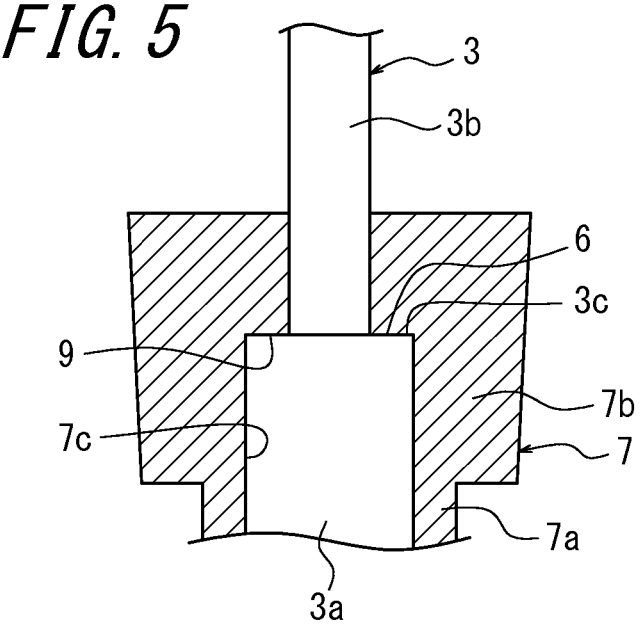
FIG. 5 is an enlarged schematic diagram illustrating a modification of the outer reduced-diameter surface and the inner reduced-diameter surface illustrated in FIG. 4.

FIG. 5 is an enlarged schematic diagram illustrating a modification of the outer reduced-diameter surface and the inner reduced-diameter surface illustrated in FIG. 4.

In FIG. 4, the inner reduced-diameter surface 9 of the inner cylindrical body 7 and the outer reduced-diameter surface 6 of the hollow needle 3 are each formed as a tapered surface, but, as illustrated in FIG. 5, the inner reduced-diameter surface 9 of the inner cylindrical body 7 and the outer reduced-diameter surface 6 of the hollow needle 3 may be each formed as a perpendicular surface perpendicular to an axial direction of the through-hole 5a. In this configuration, the inner reduced-diameter surface 9 of the inner cylindrical body 7 and the outer reduced-diameter surface 6 of the hollow needle 3 are directed in a direction of a tensile force applied to the hollow needle 3, and thus, the outer reduced-diameter surface 6 and the inner reduced-diameter surface 9 are engaged to allow the inner cylindrical body 7 to accurately support the tensile force applied to the hollow needle 3.

Note that as long as the inner reduced-diameter surface 9 of the inner cylindrical body 7 and the outer reduced-diameter surface 6 of the hollow needle 3 have shapes each having a diameter reduced toward the distal end side, and engaging with each other to lock the hollow needle 3 removed from the inner cylindrical body 7, the shapes of the inner reduced-diameter surface 9 and the outer reduced-diameter surface 6 are not limited to the conical surface illustrated in FIG. 4 or the perpendicular surface illustrated in FIG. 5, and the inner reduced-diameter surface 9 and the outer reduced-diameter surface 6 can have any shape such as a shape having an inclination angle gradually changed, arbitrarily setting the inclination angle.

Figure 6:
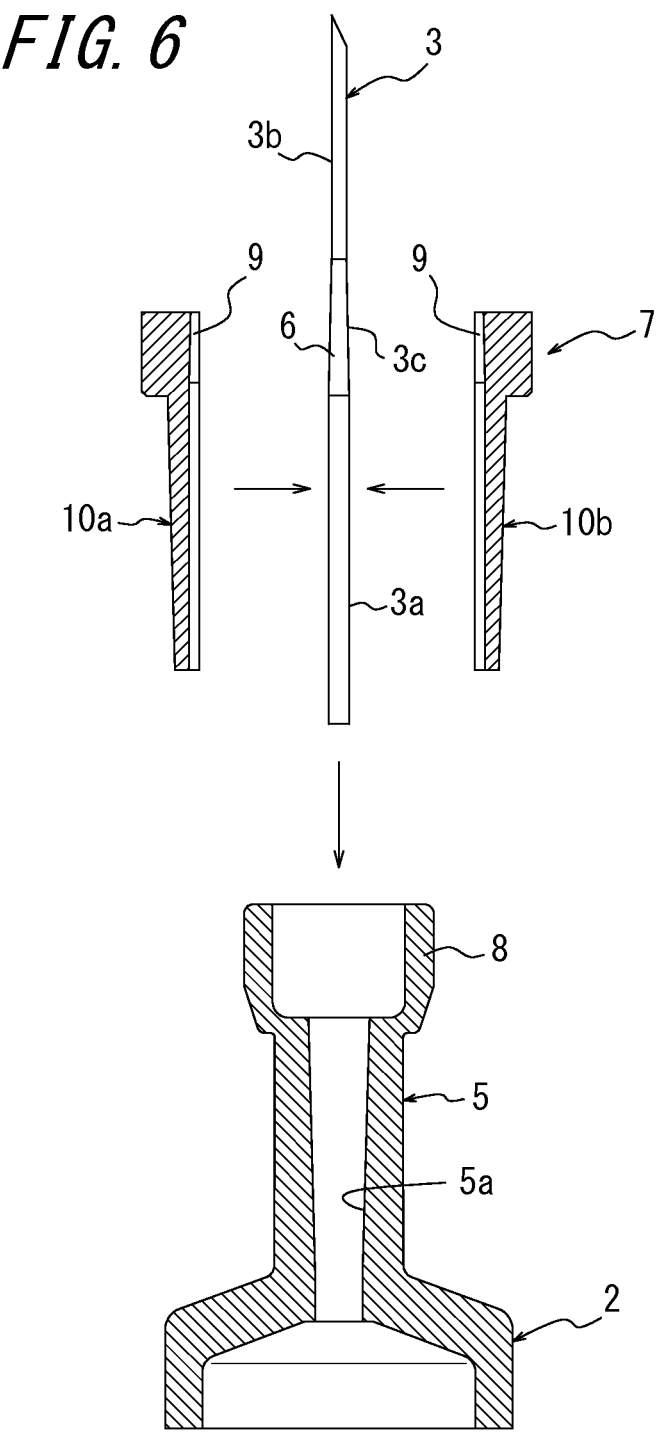
FIG. 6 is a schematic diagram of a modification of an inner cylindrical body illustrated in FIG. 2, illustrating formation of the inner cylindrical body by combining multiple segment pieces.
Figure 7:
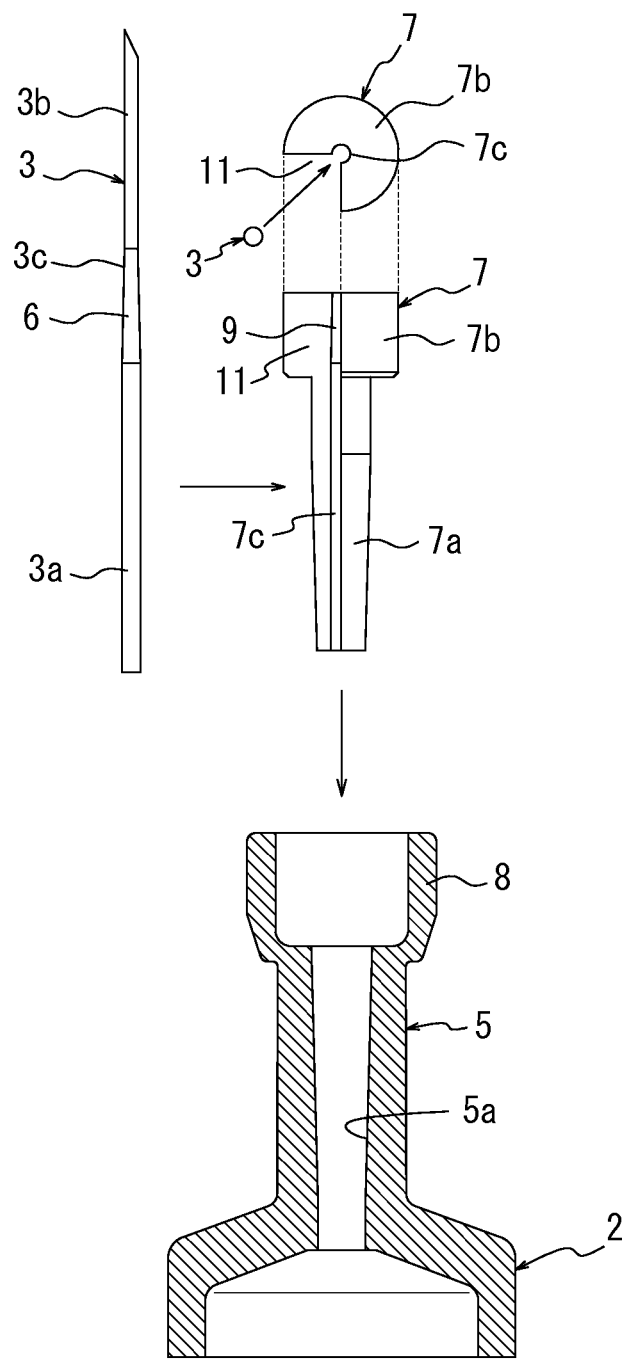
FIG. 7 is a schematic diagram of a modification of the inner cylindrical body illustrated in FIG. 2, illustrating provision of a needle insertion slit in a side portion of the inner cylindrical body.

FIG. 6 is a schematic diagram of a modification of the inner cylindrical body illustrated in FIG. 2, illustrating formation of the inner cylindrical body by combining multiple segment pieces. FIG. 7 is a schematic diagram of a modification of the inner cylindrical body illustrating in FIG. 2, illustrating provision of a needle insertion slit in a side portion of the inner cylindrical body.

In FIG. 2, the inner cylindrical body 7 is formed as a cylindrical shape, and as illustrated in FIG. 3B, the distal end of the hollow needle 3 is inserted through the insertion hole 7c of the inner cylindrical body 7.

In contrast, in the modification illustrated in FIG. 6, before the inner cylindrical body 7 is pressed into the through-hole 5a while being fused, the inner cylindrical body 7 is divided into two segment pieces 10a and 10b along a division plane passing through an axis of the insertion hole 7c and the segment pieces 10a and 10b are combined to form the cylindrical shape. Owing to such a configuration, lateral sides of the hollow needle 3 are held by the two segment pieces 10a and 10b, and the hollow needle 3 can be readily disposed in the insertion hole 7c of the inner cylindrical body 7 having a cylindrical shape, without inserting the distal end of the hollow needle 3 through the insertion hole 7c of the inner cylindrical body 7. In this configuration, while the segment pieces 10a and 10b are combined to dispose the hollow needle 3 in the insertion hole 7c of the inner cylindrical body 7, the inner cylindrical body 7 is inserted into the through-hole 5a together with the hollow needle 3. Then, in a subsequent welding step, the inner cylindrical body 7 is pressed into the through-hole 5a while being heated and fused, butted portions of the segment pieces 10a and 10b are welded and thus the inner cylindrical body 7 is formed to have a cylindrical shape. The inner cylindrical body 7 having a cylindrical shape closes between the hollow needle 3 and the inner peripheral surface of the through-hole 5a also in this configuration, thus sealing the liquid chamber of the syringe body 2.

As described above, since the inner cylindrical body 7 is divided into multiple segment pieces 10a and 10b, insertion of the hollow needle 3 into the inner cylindrical body 7 can be facilitated, and when the hollow needle 3 is inserted through the insertion hole 7c of the inner cylindrical body 7, the distal end of the hollow needle 3 can be prevented from being damaged due to sticking to the inner peripheral surface of the insertion hole 7c.

Note that, although the inner cylindrical body 7 is divided into the two segment pieces 10a and 10b, in FIG. 6, the number of divided segment pieces can be arbitrarily set, for example, the inner cylindrical body 7 can be divided into at least three segment pieces aligned in a circumferential direction about the axis of the insertion hole 7c. Furthermore, the segment pieces 10a and 10b are not limited to a configuration obtained by equally dividing the inner cylindrical body 7 in the circumferential direction, and the segment pieces 10a and 10b can be obtained by being divided in an arbitrary ratio, for example, one segment piece 10a can have an increased circumferential angle range (e.g., 270 degrees), and the other segment piece 10b can have a reduced circumferential angle range (e.g., 90 degrees).

In contrast, in the modification illustrated in FIG. 7, before the inner cylindrical body 7 is pressed into the through-hole 5a while being fused, the inner cylindrical body 7 is formed to have a C-shaped cross-section in which the needle insertion slit 11 extending from the insertion hole 7c is provided in a side portion. In FIG. 7, the inner cylindrical body 7 is formed as a shape in which a portion within a range of 90 degrees about the axis of the insertion hole 7c is notched, and the notched portion is formed as the needle insertion slit 11. Owing to such a configuration, the hollow needle 3 can be inserted from a lateral side of the inner cylindrical body 7 and disposed in the insertion hole 7c through the needle insertion slit 11, without inserting the distal end of the hollow needle 3 through the insertion hole 7c of the inner cylindrical body 7. After the hollow needle 3 is disposed in the insertion hole 7c, the inner cylindrical body 7 is inserted into the through-hole 5a together with the hollow needle 3. Then, in a subsequent welding step, the inner cylindrical body 7 is pressed into the through-hole 5a while being heated and fused, and deformed to close the needle insertion slit 11, and thus the inner cylindrical body 7 is formed to have a cylindrical shape. The inner cylindrical body 7 having a cylindrical shape closes between the hollow needle 3 and the inner peripheral surface of the through-hole 5a also in this configuration, thus sealing the liquid chamber of the syringe body 2.

Note that, in FIG. 7, the portion within the range of 90 degrees about the axis of the insertion hole 7c of the inner cylindrical body 7 is notched for the needle insertion slit 11, and the angle is arbitrarily set as long as the needle insertion slit 11 has a width large enough to insert the hollow needle 3 into the insertion hole 7c. Furthermore, the needle insertion slit 11 is not limited to the notch having a fan shape extending about the axis of the insertion hole 7c of the inner cylindrical body 7, and can have various shapes as long as the shapes allow insertion of the hollow needle 3 into the insertion hole 7c; for example, the notch can have a constant groove width.

Needless to say, the present invention is not limited to the above embodiment, and can be modified without departing from the spirit and scope of the present invention.

For example, in the above embodiment, the present invention is applied to the syringe 1 with a fixed needle for medical use, but the present invention is not limited to the above embodiment, and can be applied to another medical instrument, as long as the medical instrument has a configuration for joining the hollow metal needle to the outer cylindrical body formed of a resin, such as, an injection needle configured to join a hollow needle to a distal end of a resin hub, an indwelling needle, a butterfly needle, or a syringe with a needle used for blood sampling. In this configuration, the hub is configured as an outer cylindrical body, and can be connected to the medical instrument such as a port of a syringe body or a medical tube. A resin material for forming the hub can include, for example, polypropylene or a thermoplastic elastomer, and the inner cylindrical body can include a similar resin material.

Furthermore, in the above embodiment, the inner reduced-diameter surface 9 is provided partially on the inner peripheral surface of the inner cylindrical body 7, but the inner reduced-diameter surface 9 is not limited to the above embodiment, and is preferably provided at least partially on the inner peripheral surface of the inner cylindrical body 7, for example, the inner peripheral surface of the inner cylindrical body 7 may be wholly formed as the inner reduced-diameter surface 9. Furthermore, according to the inner reduced-diameter surface 9 of the inner cylindrical body 7, the outer reduced-diameter surface 6 provided on the outer peripheral surface of the hollow needle 3 is also preferably provided at least partially on the outer peripheral surface of the hollow needle 3, for example, the outer peripheral surface of the hollow needle 3 may be wholly formed as the outer reduced-diameter surface 6.

Furthermore, in the above embodiment, the tapered angle of the inner reduced-diameter surface 9 of the inner cylindrical body 7 and the tapered angle of the outer reduced-diameter surface 6 of the hollow needle 3 coincide with each other, but the tapered angles are not limited to the above embodiment, and can be differed as long as the outer reduced-diameter surface 6 of the hollow needle 3 can be engaged with the inner reduced-diameter surface 9 of the inner cylindrical body 7.

Furthermore, as described in the above embodiment, the inner cylindrical body 7 is preferably formed of the same resin material as the syringe body 2, but the inner cylindrical body 7 may be formed of a resin material different from that of the syringe body 2, as long as the resin material can be welded to the port 5 of the syringe body 2.

Furthermore, in the above embodiment, the hollow needle 3 is brought into close contact with the inner surface of the insertion hole 7c of the inner cylindrical body 7, without roughening, such as blasting, the outer peripheral surface of the hollow needle 3, but the outer peripheral surface of the hollow needle 3 may be roughened, for example, blasted to increase the joint strength of the hollow needle 3 to the inner peripheral surface of the insertion hole 7c.

Furthermore, the material of the outer cylindrical body and the inner cylindrical body is not limited to the resin material, and the outer cylindrical body and the inner cylindrical body may be formed of another material, for example, a metal or an elastomer. In this configuration, the inner cylindrical body may be press-fitted between the hollow needle and the inner peripheral surface of the through-hole of the outer cylindrical body.

Next, another embodiment of the present invention will be exemplified and described with reference to the drawings.

Figure 8:
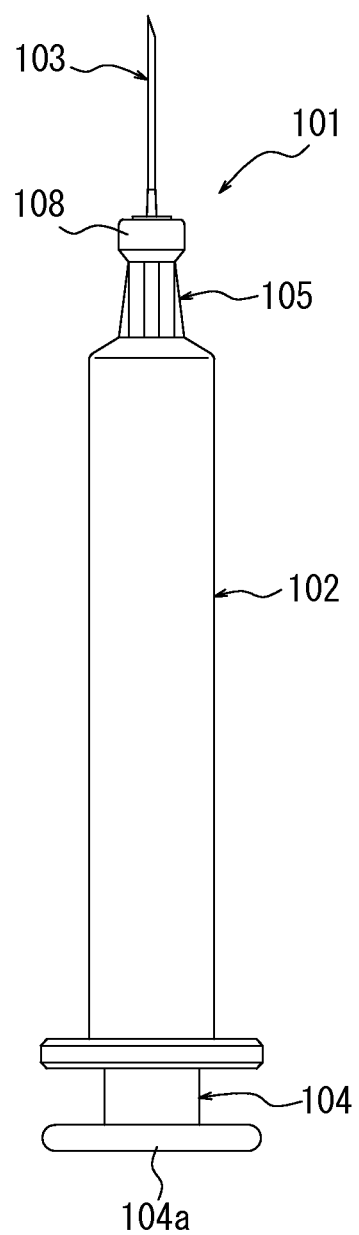
FIG. 8 is a front view of a syringe with a fixed needle which includes a hollow needle manufactured by a method of manufacturing a hollow needle according to another embodiment of the present invention.

FIG. 8 illustrate a syringe 101 with a fixed needle (medical instrument) which is used as the medical syringe for injecting a drug solution such as vaccine into a living body such as a human body, and includes a syringe body 102 and a hollow needle (cannula) 103.

The syringe body 102 is formed of a resin material, is formed as a cylindrical shape, and a piston 104 including an operation piece 104a is axially movably mounted in the syringe body 102. The inside of the syringe body 102 is partitioned by the piston 104, and defined as a liquid chamber. The liquid chamber can store the drug solution. The resin material forming the syringe body 102 can include, for example, cyclic polyolefin or polycarbonate.

Figure 9:
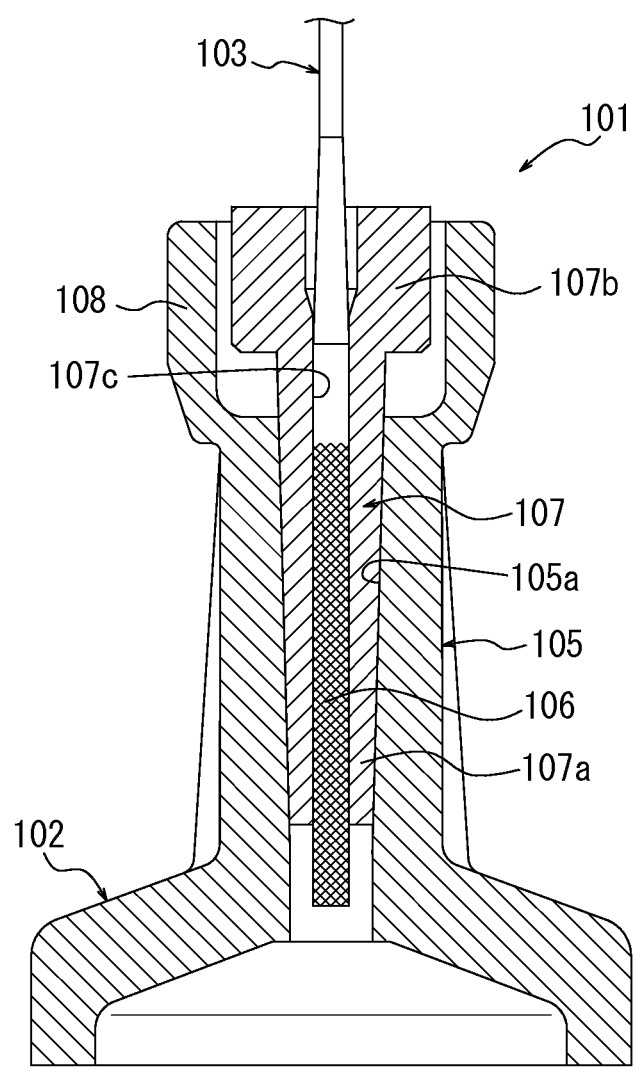
FIG. 9 is an enlarged cross-sectional view illustrating an enlarged main portion of the syringe with a fixed needle illustrated in FIG. 8.

A cylindrical port 105 serving as an outlet for a drug solution is provided at one axial end of the syringe body 102. The cylindrical port 105 is formed of the same resin as the syringe body 102, and is provided integrally with the syringe body 102. As illustrated in FIG. 9, the port 105 is axially provided with a port hole 105a, the port hole 105a extends along an axis of the syringe body 102, and is formed as a tapered hole having an inner diameter gradually reduced from a distal end side toward a proximal end side of the port 105.

Meanwhile, the hollow needle 103 is formed of a metal, is formed as an elongated tubular shape (cylindrical shape) axially including a flow channel (not illustrated), and has a distal end cut, for example, obliquely to have an acute shape to be inserted into the living body such as a human body. Furthermore, the hollow needle 103 is formed as a tapered needle having an outer diameter gradually reduced from a proximal end side toward a distal end side, and has an outer peripheral surface within a predetermined range from a proximal end of the hollow needle 103. The outer peripheral surface has a diamond knurl 106 as a roughened portion.

The hollow needle 103 is disposed coaxially with the port hole 105a, a portion on the proximal end side of the hollow needle 103 is disposed in the port hole 105a, and a portion on the distal end side projects outward from the port hole 105a. The flow channel provided in the hollow needle 103 communicates with the liquid chamber of the syringe body 102 on the proximal end side, and is opened outward on the distal end side.

A resin inner cylindrical body (cylindrical body) 107 is inserted into the port hole 105a to be positioned between an outer peripheral surface of the hollow needle 103 and an inner peripheral surface of the port hole 105a, and the hollow needle 103 is joined to the port 105 by the inner cylindrical body 107.

The inner cylindrical body 107 has a main body portion 107a having a tapered outer shape having an outer diameter gradually reduced from a distal end side (upper side in figure) toward a proximal end side (lower side in figure) thereof, and a head portion 107b provided integrally at a distal end of the main body portion 107a, and the main body portion 107a is inserted through the port hole 105a. The outer peripheral surface of the main body portion 107a is formed as a tapered surface having the same tapered angle as the inner peripheral surface of the port hole 105a, and makes contact with the inner peripheral surface of the port hole 105a. Furthermore, the inner cylindrical body 107 is axially provided with an insertion hole 107c opened at both axial ends, and the hollow needle 103 is inserted through the insertion hole 107c. The head portion 107b of the inner cylindrical body 107 is formed to have a diameter larger than that of the main body portion 107a, disposed outside the port hole 105a, and has a lower surface opposed to a distal end surface of the port 105.

The port 105 is integrally provided with a locking portion 108 for locking a rubber cover (not illustrated) covering the hollow needle 103. The locking portion 108 is formed as a cylindrical shape having a diameter larger than that of the port 105, projects axially upward from the distal end of the port 105, and covers an outer periphery of the head portion 107b of the inner cylindrical body 107 inserted through the port hole 105a. The syringe body 102 may have a configuration in which the port 105 is not provided with the locking portion 108.

The main body portion 107a of the inner cylindrical body 107 is pressed into the port hole 105a, that is, between the hollow needle 103 and the inner peripheral surface of the port hole 105a while being heated and fused. Thus, in the inner cylindrical body 107, the outer peripheral surface of the main body portion 107a is welded on the inner peripheral surface of the port hole 105a, an inner peripheral surface of the insertion hole 107c of the main body portion 107a makes close contact with the outer peripheral surface of the hollow needle 103, and the port 105 and the hollow needle 103 are joined to each other. At this time, in the hollow needle 103, the outer peripheral surface of the hollow needle 103 having the diamond knurl 106 is joined to the inner peripheral surface of the insertion hole 107c. In this configuration, the main body portion 107a of the inner cylindrical body 107 can be pressed between the hollow needle 103 and the inner peripheral surface of the port hole 105a while being fused, for example, according to the following procedure.

First, as illustrated in FIG. 10A, the main body portion 107a of the inner cylindrical body 107 is inserted through the port hole 105a, next, as illustrated in FIG. 10B, the hollow needle 103 is inserted from above through the insertion hole 107c of the inner cylindrical body 107 inserted through the port hole 105a, and a proximal end portion of the hollow needle 103 is held at a predetermined position by a fixture or the like. As illustrated in FIG. 10C, an upper surface of the head portion 107b is pressed toward the port hole 105a by the pressing device or the like, while heating the main body portion 107a and the port 105, and the main body portion 107a of the inner cylindrical body 107 is pressed between the hollow needle 103 and the inner peripheral surface of the port hole 105a, while being fused. Thus, in the inner cylindrical body 107, the outer peripheral surface of the main body portion 107a is welded on the inner peripheral surface of the port hole 105a, an inner peripheral surface of the insertion hole 107c makes close contact with the outer peripheral surface of the hollow needle 103 having the diamond knurl 106 to generate the anchor effect, and the port 105 and the hollow needle 103 can be joined to each other. At this time, since the port hole 105a and the main body portion 107a of the inner cylindrical body 107 are formed as the tapered shape, the diameter of the main body portion 107a is gradually reduced as the pressing progresses. Thus, the main body portion 107a of the inner cylindrical body 107 can be firmly joined to an inner surface of the port hole 105a or the outer peripheral surface of the hollow needle 103 having the diamond knurl 106. Note that, in the inner cylindrical body 107, at least part of the outer peripheral surface of the main body portion 107a is preferably welded on the inner peripheral surface of the port hole 105a, and a welding range or welding position thereof can be arbitrarily set.

In the above method, the inner cylindrical body 107 and the port 105 can be heated for example by laser radiation. In this configuration, the hollow needle 103 including the metal is heated by the laser, and then the inner cylindrical body 107 and the port 105 are heated by heat transferred from the hollow needle 103. In the present embodiment, as indicated by a portion enclosed by a dashed line in FIG. 10C, the main body portion 107a pressed between the port 105 and the port hole 105a is heated within a range of approximately 3 mm from an opening of the port hole 105a.

Note that a filler including a heat generating material such as a metal may be mixed, or a ring member including the heat generating material such as a metal may be disposed, in the inner cylindrical body 107 or the port 105 to directly heat the inner cylindrical body 107 or the port 105 by laser radiation. Furthermore, means for heating is not limited to laser radiation, and may employ other means, for example, ultrasonic heating or high-frequency heating. Furthermore, a configuration may be employed in which only the inner cylindrical body 107 is heated and the port 105 is not heated.

As described above, while the hollow needle 103 is located at a predetermined position in the port hole 105a, the inner cylindrical body 107 receiving the insertion of the hollow needle 103 is pressed between the hollow needle 103 and the inner peripheral surface of the port hole 105a, while being heated and fused by the laser radiation. Thus, the outer peripheral surface of the inner cylindrical body 107 can be accurately welded on the inner peripheral surface of the port hole 105a. Furthermore, the outer peripheral surface of the hollow needle 103 has the diamond knurl 106, the inner peripheral surface of the insertion hole 107c of the inner cylindrical body 107 is brought into close contact with the outer peripheral surface of the hollow needle 103 having the diamond knurl 106 to smooth slight roughness on the outer peripheral surface, and thus an inner peripheral surface of the inner cylindrical body 107 can be firmly joined to the outer peripheral surface of the hollow needle 103 by the anchor effect. Accordingly, the hollow needle 103 is firmly joined to the port 105 through the inner cylindrical body 107.

Note that, as described above, a process of pressing the inner cylindrical body 107 while heating and fusing allows joining without generating bubbles in the inner cylindrical body 107. Accordingly, the inner cylindrical body 107 accurately fills a gap between the outer peripheral surface of the hollow needle 103 and the inner peripheral surface of the port hole 105a, and the liquid chamber of the syringe body 102 can be sealed.

The hollow needle 103 used for the syringe with a fixed needle having such a configuration can be manufactured by a method of manufacturing a hollow needle according to an embodiment of the present invention. The method of manufacturing a hollow needle according to an embodiment of the present invention includes a pressing step and a joining step. The method will be described below.

First, in the pressing step, a plate body 110 is punched out from a metal plate including a stainless steel, a titanium alloy, or the like being a material of the hollow needle 103, by pressing using a punching die. As illustrated on the top left side of FIG. 11, the plate body 110 is formed as a predetermined shape having a small width on the distal end side and a large width on the proximal end side, corresponding to a developed shape of the hollow needle 103.

Furthermore, in the pressing for punching out the plate body 110, a surface of the plate body 110 is roughened simultaneously with the punching. That is, a surface of a portion of the punching die punching out the metal plate is provided with a roughening portion having a roughened surface, the roughening portion is strongly pressed against a surface of the metal plate when punching out the metal plate, and the diamond knurl 106 as the roughened portion is formed on the surface of the plate body 110 punched out from the metal plate. As described above, in the present embodiment, when punching out the plate body 110 from the metal plate, the diamond knurl 106 can be formed on the surface of the plate body 110, in the same step using the same die used for punching out the plate body 110.

Figure 11:
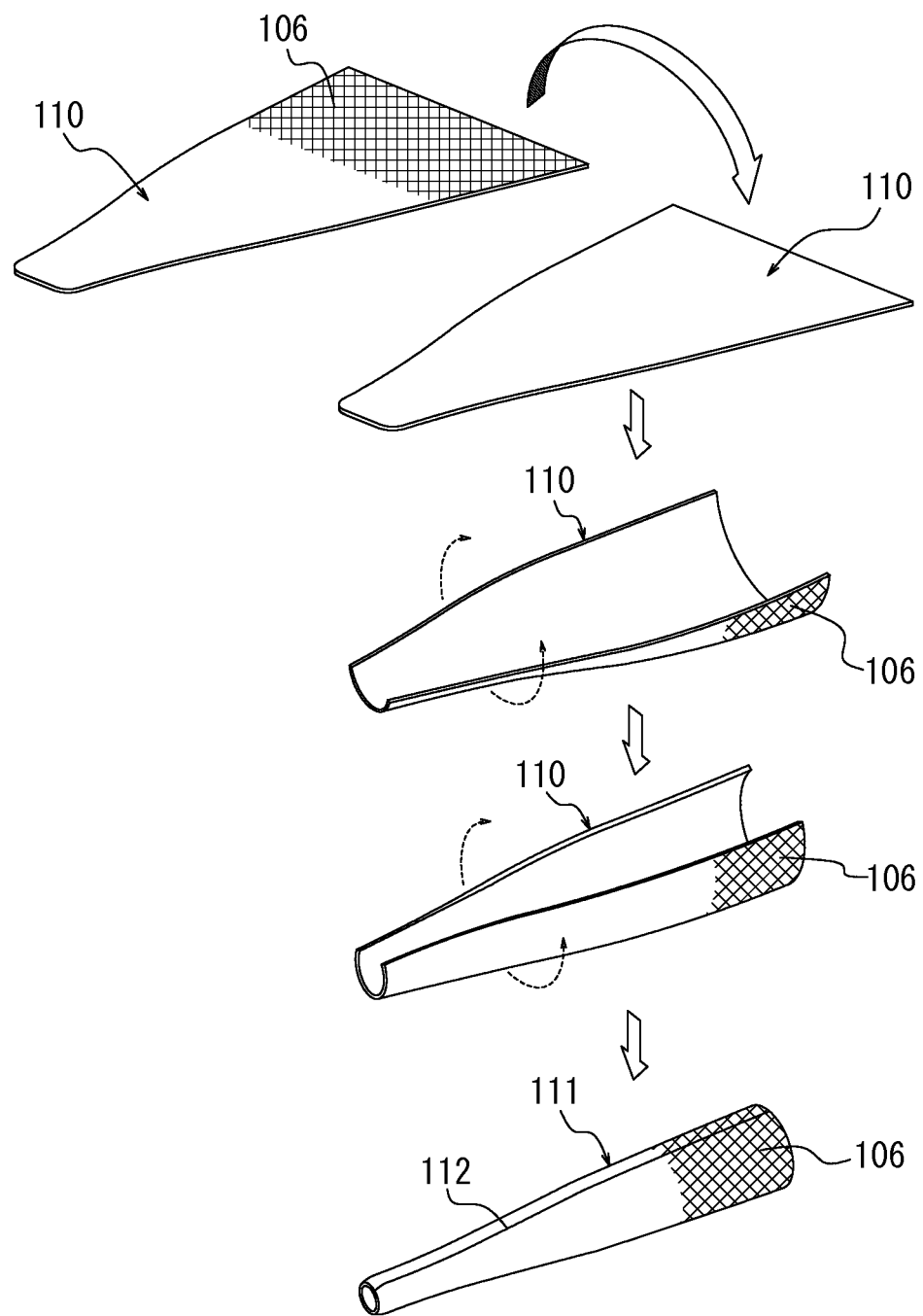
FIG. 11 is a schematic diagram illustrating a procedure of a method of manufacturing a hollow needle illustrated in FIG. 8.

In the pressing step, next, the plate body 110 having the diamond knurl 106 on the surface is sequentially rolled so that the surface having the diamond knurl 106 thereon is positioned on the surface side, and molded into a tubular body 111, as illustrated on the right side of FIG. 11. Molding of the plate body 110 into the tubular body 111 can be performed for example, using molds 121 to 123, as illustrated in FIGS. 12A and 12B.

Figure 12A:
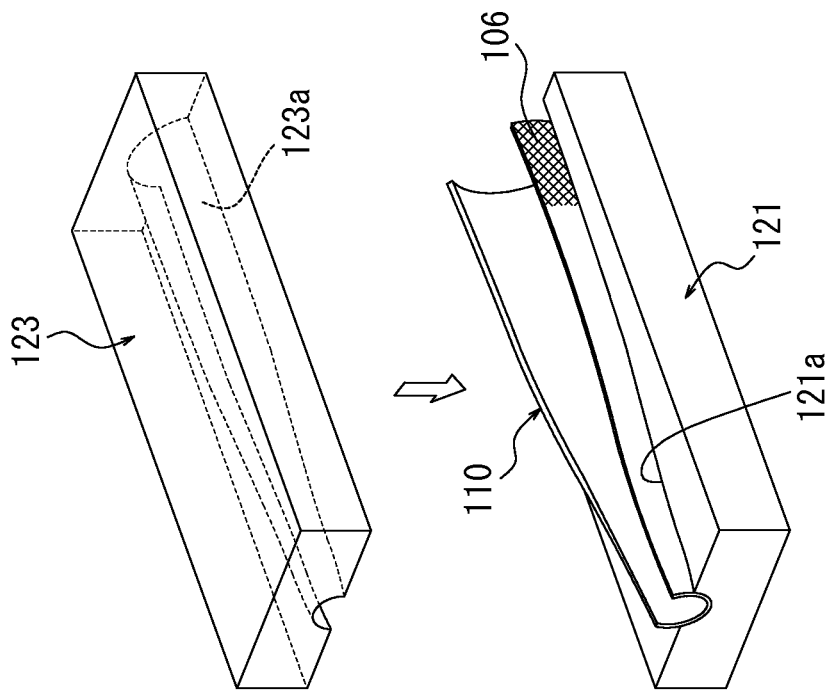
FIGS. 12A and 12B are schematic diagrams illustrating a procedure of rolling a plate body into a tubular shape in FIG. 11.
Figure 12B:
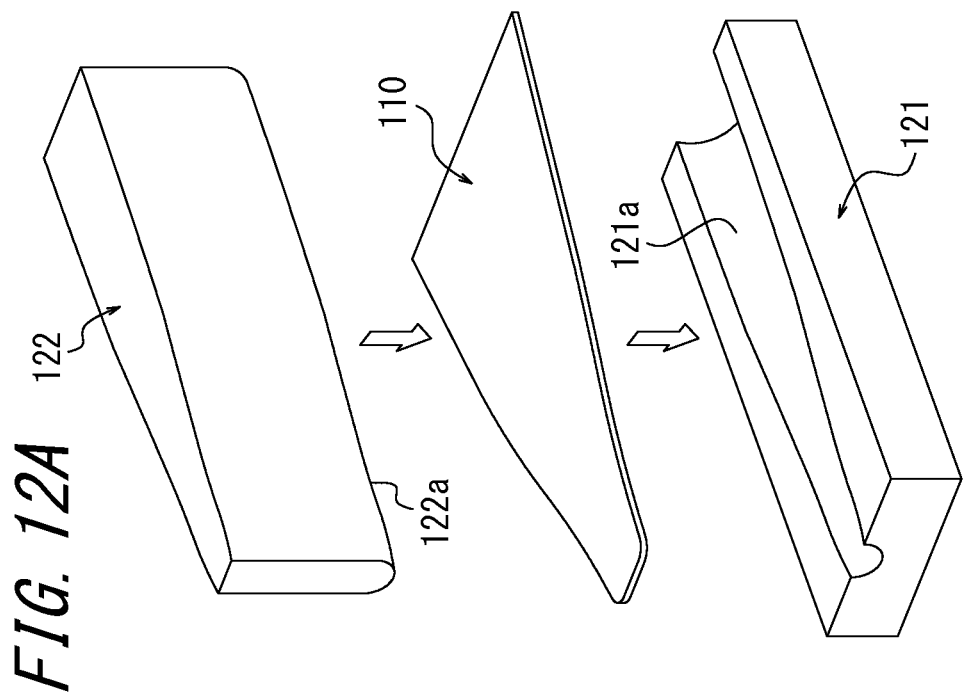

As illustrated in FIG. 12A, in the molding, the plate body 110 is disposed in the mold 121 as a lower mold, pressed into a recessed portion 121a of the mold 121 by a projecting portion 122a of the mold 122 as an upper mold, and bent into a U-shaped cross-section. Next, as illustrated in FIG. 12B, the mold 123 including a recessed portion 123a is used as the upper mold to bend the remaining portion of the plate body 110. Thus, the plate body 110 is molded into the tubular body 111.

When the plate body 110 is rolled and molded into the tubular body 111, the joining step is performed next. In the joining step, as illustrated on the bottom right side of FIG. 11, a seam portion 112 of the tubular body 111, that is, butted side end surfaces of the rolled plate body 110 are joined by welding or with an adhesive material. At the end of the joining step, the seam portion 112 of the plate body 110 is joined, and the hollow needle 103 is completed.

Figure 13B:
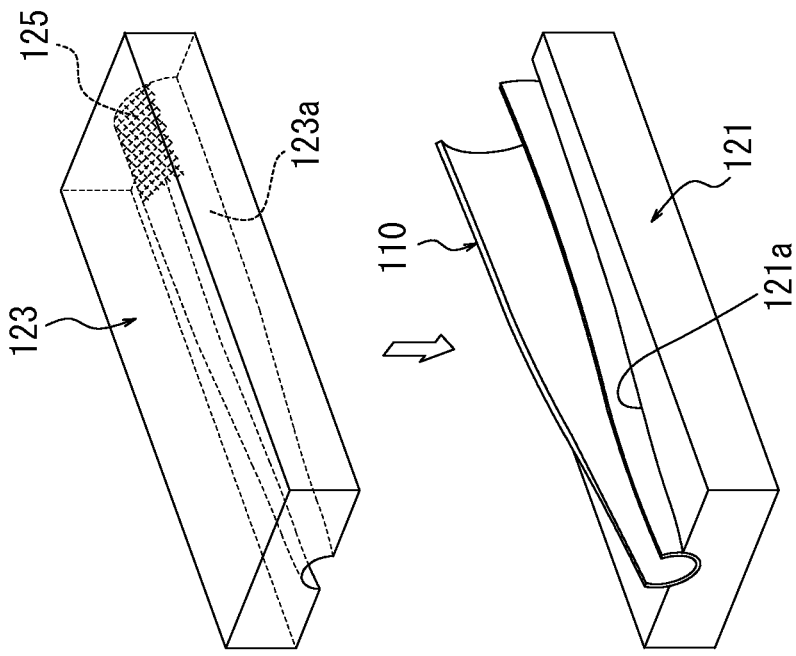
FIGS. 13A and 13B are schematic diagrams of a modification of the method of manufacturing a hollow needle illustrated in FIG. 11, illustrating a procedure of roughening a surface of a plate body upon rolling the plate body into a tubular shape.
Figure 13A:
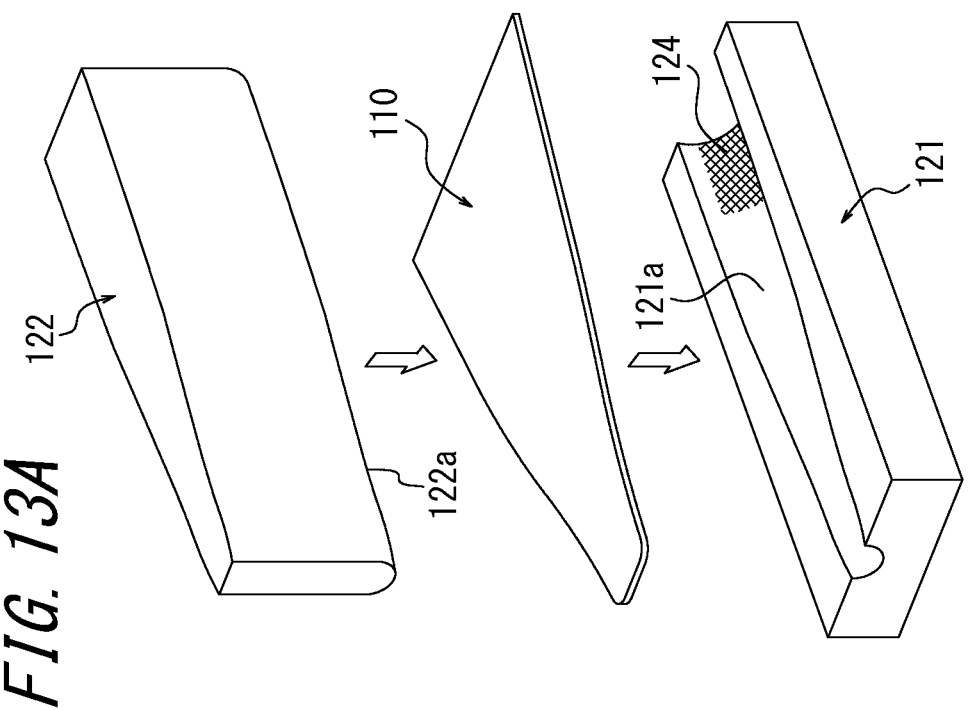

FIGS. 13A and 13B are schematic diagrams of a modification of the method of manufacturing a hollow needle illustrated in FIG. 11, illustrating a procedure of roughening the surface of the plate body upon rolling the plate body into the tubular shape.

In the above embodiment, when punching out the plate body 110 from the metal plate in the pressing step, the surface of the plate body 110 is roughened, but, as illustrated in FIGS. 13A and 13B, the plate body 110 may be also configured so that when punching out the plate body 110, the plate body 110 is not roughened, and when rolling the plate body 110 punched out from the metal plate into the tubular shape to be molded into the tubular body 111, the surface of the plate body 110 is roughened.

In this configuration, as illustrated in FIG. 13, an inner surface of the recessed portion 121a of the mold 121 as the lower mold is provided with a rough surface forming portion 124 having a roughened surface, and an inner surface of the recessed portion 123a of the mold 123 as the upper mold is provided with a rough surface forming portion 125 having a roughened surface. As illustrated in FIG. 13A, in molding, when the plate body 110 is disposed in the mold 121 as the lower mold, pressed in the recessed portion 121a of the mold 121 by the projecting portion 122a of the mold 122 as the upper mold, and bent into the U-shaped cross-section, the rough surface forming portion 124 is strongly pressed against the surface of the plate body 110, and the diamond knurl 106 is formed on the surface of the plate body 110. Next, as illustrated in FIG. 13B, when the remaining portion of the plate body 110 is bent with the mold 123 including the recessed portion 123a as the upper mold, the rough surface forming portion 125 is strongly pressed against the surface of the plate body 110, and the diamond knurl 106 is formed on the surface of the plate body 110. The seam portion 112 of the tubular body 111 thus molded is joined in the joining step, thus manufacturing the hollow needle 103 having the outer peripheral surface provided with the diamond knurl 106.

Note that, in FIG. 13, the rough surface forming portion 124 provided in the recessed portion 121a of the mold 121 is formed only on the inner surface within a predetermined range of a portion of the recessed portion 121a having a larger depth, and the rough surface forming portion 125 provided in the recessed portion 123a of the mold 123 is formed only on the inner surface within a predetermined range of a portion of the recessed portion 123a having a larger depth. Thus, after the molding, the tubular body 111 having an outer peripheral surface on which the diamond knurl 106 is formed can be readily removed from the recessed portions 121a and 123a of the molds 121 and 123.

As described above, in the pressing step, the plate body 110 having a surface formed with the diamond knurl 106 is punched out from the metal plate, the plate body 110 is rolled to be molded into the tubular body 111, and in the joining step, the seam portion 112 of the tubular body 111 is joined, and thus, the hollow needle 103 of tubular shape can be manufactured which is provided with the diamond knurl 106 on the outer peripheral surface within the predetermined range of the proximal end side. That is, in this embodiment, the pressing step is configured so that the roughening is performed simultaneously with the pressing using the same die in the same step, and thus, the diamond knurl 106 can be provided on the outer peripheral surface of the hollow needle 103. Thus, another step of providing the diamond knurl 106 on the outer peripheral surface of the hollow needle 103 is not required, and the manufacturing process of the hollow needle 103 can be simplified. Furthermore, the diamond knurl 106 can be provided on the outer peripheral surface of the hollow needle 103 without blasting in the pressing step, thus preventing the attachment of the foreign matter, such as a projection material used for the blasting or broken pieces caused by the blasting, to the hollow needle 103 being completed.

Needless to say, the present invention is not limited to the above embodiment, and can be modified without departing from the spirit and scope of the present invention.

Figure 14A:
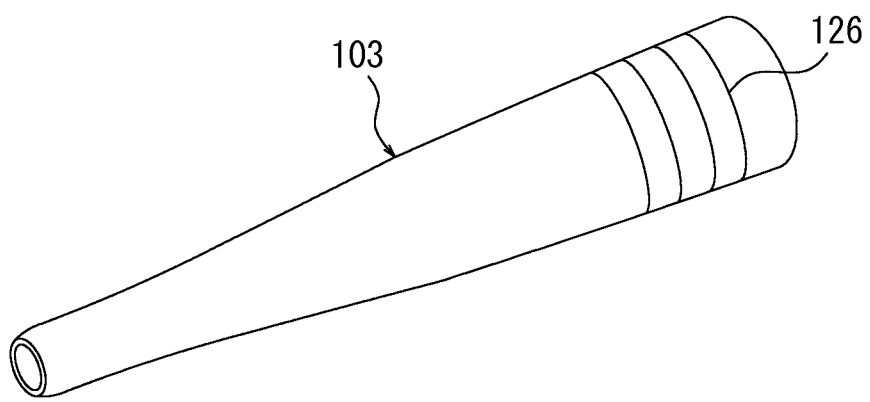
FIGS. 14A and 14B are perspective views of modifications of a hollow needle illustrated in FIG. 9.

For example, in the hollow needle 103 illustrated in FIG. 9, the roughened portion provided on the outer peripheral surface of the hollow needle 103 is formed as the diamond knurl 106, but the roughened portion may have various forms. In FIG. 14A, a roughened portion 126 is illustrated, the roughened portion 126 being formed as an elongated annular groove extending along a circumferential direction of the outer peripheral surface of the hollow needle 103. In this configuration, the number of roughened portions 126 formed as the annular grooves are not limited to four, and at least one roughened portion 126 is preferably provided.

Figure 14B:
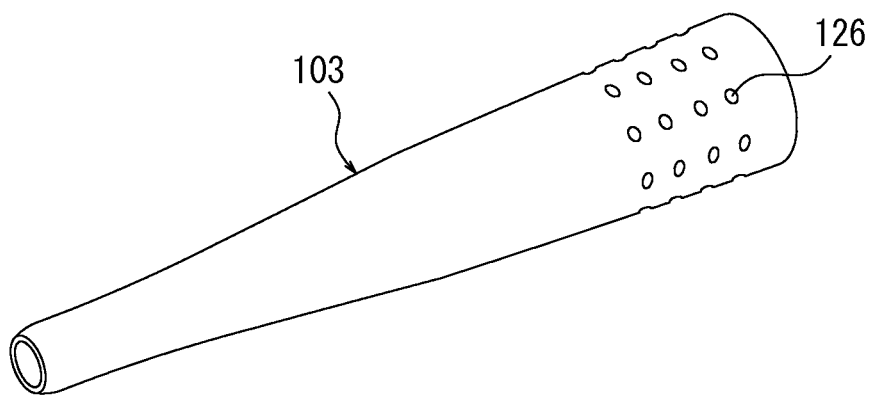

Furthermore, as illustrated in FIG. 14B, the roughened portions 126 may be formed as a large number of recesses recessed relative to the outer peripheral surface of the hollow needle 103. In this configuration, the roughened portion 126 formed as a recess may be arbitrarily set in number, size, or the like.

Figure 15:
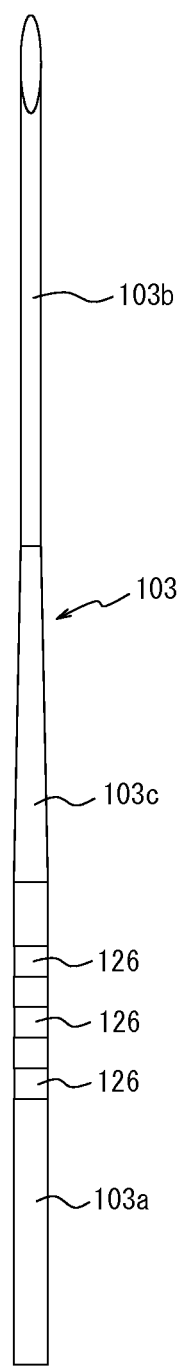
FIG. 15 is a front view of a modification of the hollow needle illustrated in FIG. 9.

Furthermore, for example, as illustrated in FIG. 15, a wide annular groove extending along a circumferential direction of the hollow needle 103 may be formed, as the roughened portion 126, on the outer peripheral surface of the hollow needle 103, that is, the annular groove has a width (dimension along an axial direction of the hollow needle 3) being sufficiently larger than a depth (radial dimension from the outer peripheral surface of the hollow needle 3 to a bottom surface of the roughened portion 126). In FIG. 15, the hollow needle 103 is illustrated which is formed as a tapered needle having a large diameter portion 103a, a small diameter portion 103b, and a reduced-diameter portion 103c. In the hollow needle 103, a portion within a predetermined range from the proximal end of the hollow needle 103 is defined as the large diameter portion 103a having a constant outer diameter, a portion within a predetermined range from the distal end is defined as the small diameter portion 103b having a constant outer diameter smaller than that of the large diameter portion 103a, and a portion between the large diameter portion 103a and the small diameter portion 103b is defined as the reduced-diameter portion 103c formed as a tapered surface shape (conical surface shape), having an outer diameter gradually reduced from the proximal end side toward the distal end side. Further, the large diameter portion 103a has an outer peripheral surface on which three roughened portions 126 each formed as the wide annular groove are axially arranged at equal intervals. In this configuration, the three roughened portions 126 are formed as groove shapes having equal widths and depths, and each having the bottom surface formed as a cylindrical surface parallel with the outer peripheral surface of the hollow needle 103, and are axially arranged at an interval of twice the width thereof. Note that, in FIG. 15, the large diameter portion 103a has an outer diameter of 0.56 mm, the roughened portion 126 has a width of 0.5 mm, and the roughened portion 126 has a depth of 0.01 mm.

As described above, in the configuration in which the roughened portion 126 is formed on the outer peripheral surface of the hollow needle 103, into the wide annular groove extending along the circumferential direction of the hollow needle 103, the inner cylindrical body 107 is fused by being heated by laser radiation or the like, and pressed between the hollow needle 103 and the inner peripheral surface of the port hole 105a, the inner cylindrical body 107 enters the roughened portions 126 to fill the roughened portions 126, and portions of the inner cylindrical body 107 entering the roughened portions 126 and side surface portions of the roughened portions 126 are axially engaged to each other. Thus, the hollow needle 103 is locked to the inner cylindrical body 107 in a removal direction (axial direction), and the joint strength of the hollow needle 103 to the inner cylindrical body 107 can be increased relative to the tensile load.

Figure 16A:
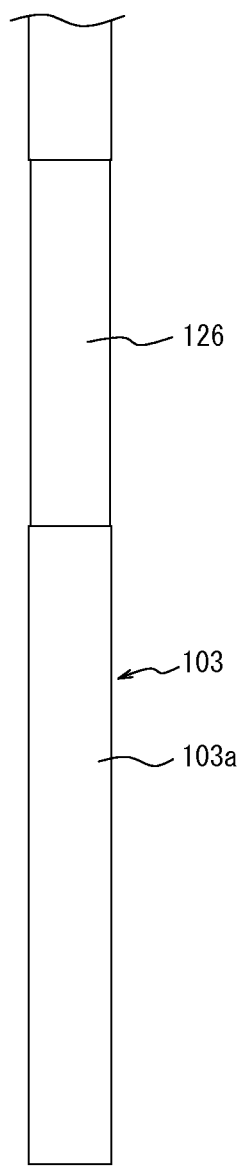
FIGS. 16A to 16C are front views of modifications of disposition of a roughened portion illustrated in FIG. 15.
Figure 16B:
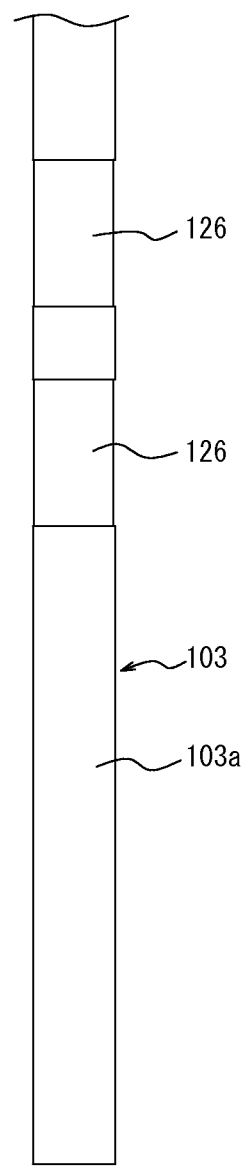

In a modification as shown in FIG. 15, the three roughened portions 126 each formed as the wide annular groove are illustrated which are provided on the outer peripheral surface of the large diameter portion 103a of the hollow needle 103 to be axially arranged at equal intervals, but the number of roughened portions 126 provided on the outer peripheral surface of the large diameter portion 103a may be set arbitrarily, for example, one roughened portion 126 may be provided on the outer peripheral surface of the large diameter portion 103a of the hollow needle 103, as illustrated in FIG. 16A, or for example, two roughened portions 126 having an equal width may be axially arranged on the outer peripheral surface of the large diameter portion 103a of the hollow needle 103, as illustrated in FIG. 16B. In these configurations, engagement between a portion of the inner cylindrical body 107 entering the roughened portion 126 and the side surface portions of the roughened portion 126 also locks the hollow needle 103 to the inner cylindrical body 107 in the removal direction, and the joint strength of the hollow needle 103 to the inner cylindrical body 107 can be effectively increased relative to the tensile load.

Figure 16C:
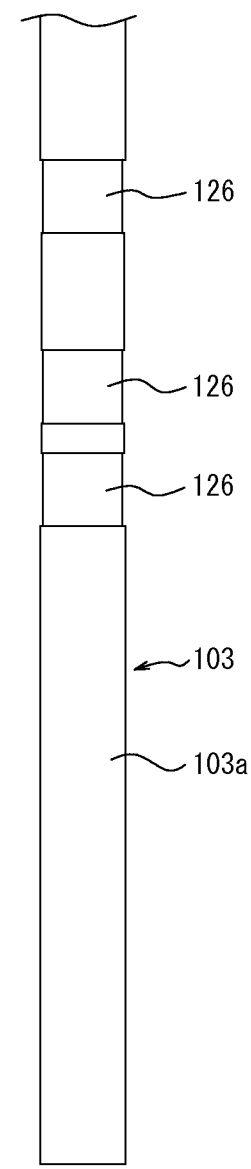

Furthermore, for example as illustrated in FIG. 16C, at least three roughened portions 126 (three roughened portions in FIG. 16C) having an equal width may be axially arranged on the outer peripheral surface of the hollow needle 103, at different intervals (irregular pitch). In this configuration, similarly to the above, engagement between the portions of the inner cylindrical body 107 entering the roughened portions 126 and the side surface portions of the corresponding roughened portions 126 also locks the hollow needle 103 to the inner cylindrical body 107 in the removal direction, and the joint strength of the hollow needle 103 to the inner cylindrical body 107 can be effectively increased relative to the tensile load.

The wide annular groove (roughened portion 126) extending in the circumferential direction of the outer peripheral surface of the hollow needle 103 preferably has a depth of 4 to 20 μm, more preferably 6 to 14 μm.

Furthermore, the diamond knurl 106 is not limited to the one provided over the whole circumference of the hollow needle 103, and the diamond knurl 106 may be provided at least partially on an outer peripheral surface of a portion of the hollow needle 103 joined to the inner peripheral surface of the insertion hole 107c of the inner cylindrical body 107, for example, the diamond knurl 106 may be provided only partially on the whole circumference of the hollow needle 103, or may be provided intermittently in the circumferential direction.

Furthermore, in the above embodiment, the hollow needle 103 manufactured by the method of manufacturing a hollow needle according to the present invention is applied to the syringe 101 with a fixed needle for medical use, but the present invention is not limited to the above embodiment, and can be applied to another medical instrument, such as, an injection needle configured to join a hollow needle to a distal end of a resin hub, an indwelling needle, a butterfly needle, or a syringe with a needle used for blood sampling.

Furthermore, in the above embodiment, the inner cylindrical body 107 is formed as the cylindrical body, and the hollow needle 103 manufactured by the method of manufacturing a hollow needle according to the present invention is formed to be joined to the inner peripheral surface of the insertion hole 107c of the inner cylindrical body 107, but the port 105 of the syringe body 102 may be formed as a cylindrical body, and the hollow needle 103 manufactured by the method of manufacturing a hollow needle according to an embodiment the present invention may be formed to be directly joined to the inner peripheral surface of the port hole 105a.

REFERENCE SIGNS LIST 1 syringe with a fixed needle (medical hollow needle assembly)
2 syringe body
3 hollow needle
3a large diameter portion
3b small diameter portion
3c reduced-diameter portion
4 piston
4a operation piece
5 port (outer cylindrical body)
5a through-hole
6 outer reduced-diameter surface
7 inner cylindrical body
7a main body portion
7b head portion
7c insertion hole
8 locking portion
9 inner reduced-diameter surface
10a segment piece
10b segment piece
11 needle insertion slit
101 syringe with a fixed needle (medical instrument)
102 syringe body
103 hollow needle
103a large diameter portion
103b small diameter portion
103c reduced-diameter portion
104 piston
104a operation piece
105 port
105a port hole
106 diamond knurl (roughened portion)
107 inner cylindrical body (cylindrical body)
107a main body portion
107b head portion
107c insertion hole
108 locking portion
110 plate body
111 tubular body
112 seam portion
121 mold
121a recessed portion
122 mold
122a projecting portion
123 mold
123a recessed portion
124, 125 rough surface forming portion
126 roughened portion

What is claimed is:

1. A method of manufacturing a medical instrument that comprises a cylindrical body, and a hollow needle formed of metal and joined to an inner peripheral surface of the cylindrical body, the method comprising:
providing the hollow needle, which comprises one or more annular grooves extending in a circumferential direction of the hollow needle at a proximal portion of the hollow needle, wherein the step of providing the hollow needle comprises:
punching out a plate body having a predetermined shape from a metal plate and rolling the plate body into a tubular shape, and
joining a seam portion of the plate body that has been rolled into the tubular shape so as to form the hollow needle,
wherein the one or more annular grooves are formed during the steps of punching out the plate body from a metal plate and rolling the plate body into the tubular shape; and
axially engaging a side surface portion of each of the one or more annular grooves and a portion of the inner peripheral surface of the cylindrical body that enters into the annular groove to each other so as to join the hollow needle and the cylindrical body.

2. The method according to claim 1,
wherein one or more grooves that will become the one or more annular grooves are formed when the plate body is punched out from the metal plate.

3. The method according to claim 1,
wherein one or more grooves that will become the one or more annular grooves are formed when the plate body is rolled into the tubular shape.

4. The method according to claim 1,
wherein the one or more annular grooves comprise a plurality of annular grooves located at intervals in an axial direction of the hollow needle.

5. The method according to claim 1,
wherein each of the one or more annular grooves has a depth in a range of 4 to 20 µm.

6. The method according to claim 1,
wherein each of the one or more annular grooves has a depth in a range of 6 to 14 µm.

7. The method according to claim 1,
wherein the hollow needle comprises:
a large diameter portion disposed at proximal end portion of the hollow needle,
a small diameter portion disposed at distal end portion of the hollow needle, wherein an outer diameter of the small diameter portion is smaller than an outer diameter of the large diameter portion, and
a reduced-diameter portion disposed between the large diameter portion and the small diameter portion, and including a tapered surface that has an outer diameter gradually reduced from a proximal end of the reduced-diameter portion toward a distal end of the reduced-diameter portion; and
wherein the one or more annular grooves are formed at an outer peripheral surface of the large diameter-portion.

8. The method according to claim 1,
wherein the medical instrument is a syringe that comprises:
a syringe body formed of a resin material,
the cylindrical body disposed at a distal end of the syringe body, and
the hollow needle joined to the syringe body via the cylindrical body.

9. The method according to claim 1, wherein the cylindrical body is heated during the step of axially engaging a side surface portion of each of the one or more annular grooves and a portion of the cylindrical body that enters into the annular groove to each other.

10. The method according to claim 1, wherein the cylindrical body is heated by laser radiation during the step of axially engaging a side surface portion of each of the one or more annular grooves and a portion of the cylindrical body that enters into the annular groove to each other.

\* \* \* \* \*